United States Patent [19]

Small, Jr.

[11] 4,394,277
[45] Jul. 19, 1983

[54] METHOD FOR IMPROVING FUEL ECONOMY OF INTERNAL COMBUSTION ENGINES USING BORATED SULFUR-CONTAINING 1,2-ALKANE DIOLS

[75] Inventor: Vernon R. Small, Jr., Rodeo, Calif.

[73] Assignee: Chevron Research Company, San Francisco, Calif.

[21] Appl. No.: 314,631

[22] Filed: Oct. 26, 1981

[51] Int. Cl.³ .......................... C10M 1/54; C10M 1/38
[52] U.S. Cl. ............................... 252/32.7 E; 252/48.2; 252/48.4; 252/49.6
[58] Field of Search ................ 252/32.7 E, 48.4, 49.6, 252/48.2, 25; 568/46, 6

[56] References Cited

U.S. PATENT DOCUMENTS

| | | | |
|---|---|---|---|
| 2,795,548 | 6/1957 | Thomas et al. | 252/49.6 |
| 2,894,020 | 7/1959 | McManimie | 252/49.6 |
| 3,076,013 | 1/1963 | Liao et al. | 252/49.6 |
| 3,347,790 | 10/1967 | Meinhardt | 252/32.7 E |
| 3,562,159 | 2/1971 | Mastin | 252/32.7 E |

Primary Examiner—Jacqueline V. Howard
Attorney, Agent, or Firm—D. A. Newell; J. M. Whitney; V. J. Cavalieri

[57] ABSTRACT

Lubricating oils containing borated sulfur-containing 1,2-alkane diols have been found to reduce fuel consumption in an internal combustion engine.

19 Claims, No Drawings

METHOD FOR IMPROVING FUEL ECONOMY OF INTERNAL COMBUSTION ENGINES USING BORATED SULFUR-CONTAINING 1,2-ALKANE DIOLS

FIELD OF THE INVENTION

This invention relates to lubricating oil compositions and their use in reducing fuel consumption in internal combustion engines. More particularly, it deals with crankcase lubricating oil compositions containing borated sulfur-containing 1,2-alkane diols as friction reducing agents.

BACKGROUND OF THE INVENTION

With the crisis associated with diminishing amounts of fossil fuel and the rapidly increasing prices for this fuel, there has been a great deal of interest in reducing the amount of fuel consumed by automobile engines, and the like.

Thus, there is a great need to find lubricants that reduce the overall friction in the engine, thus reducing the energy requirements thereto.

U.S. Pat. No. 4,201,684 teaches lubricating oils containing sulfurized fatty acid amides, esters or ester-amides of alkoxylated amines, which reduce friction between sliding metal surfaces in internal combustion engines.

U.S. Pat. No. 4,209,410 teaches lubricating oils containing hydroxyalkyl sulfides. The additives are taught to improve the anti-wear properties of the resulting compositions.

U.S. Pat. No. 4,225,449 teaches lubricating oils containing aliphatic hydrocarbylsulfonylalkanol or aliphatic hydrocarbylsulfinylalkanols, which reduce friction resulting in improved fuel economy in internal combustion engines.

Lubricating oil compositions as herein described possess excellent oxidation and corrosion inhibiting properties as well as excellent dispersion, wear and frictional properties.

It has now been found that lubricating the crankcase of an internal combustion engine with a lubricating oil containing borated sulfur-containing 1,2-alkane diols reduce the fuel consumption of the engine.

SUMMARY OF THE INVENTION

According to the present invention, lubricating oils are provided which reduce friction between sliding metal surfaces in the crankcase of internal combustion engines. The reduced friction is a result of the addition to the lubricating oil of effective amounts of a borated sulfur-containing 1,2-alkane diol of the formula

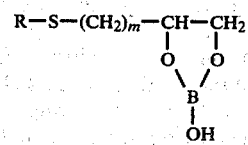

wherein R is alkyl containing from 5 to 30 carbon atoms, and m is 1 or 2 and mixtures thereof. Preferably said alkyl is linear and contains little or no branching, and m is 1. Most preferably R contains from 5 to 18 carbon atoms.

Other additives may also be present in the lubricating oil in order to obtain a proper balance of properties such as dispersion, corrosion, wear and oxidation which are critical for the proper operation of an internal combustion engine.

Thus, another embodiment of the present invention is directed to a lubricating oil formulated for use in the crankcase of an internal combustion engine for the purpose of improving the fuel consumption of said engine comprising (a) a major amount of an oil of lubricating viscosity; and (b) an effective amount of each of the following:
1. an alkenyl succinimide or succinate or mixtures thereof,
2. a Group II metal salt of a dihydrocarbyl dithiophosphoric acid,
3. a neutral or overbased alkali or alkaline earth metal hydrocarbyl sulfonate or mixtures thereof,
4. a neutral or overbased alkali or alkaline earth metal alkylated phenate, or mixtures thereof, and
5. a borated sulfur-containing 1,2-alkane diol friction modifier of the Formula I described hereinabove.

Further, in accordance with the invention, there is provided a method for reducing fuel consumption of an internal combustion engine by treating the moving surfaces thereof with the lubricating oil containing the borated sulfur-containing friction modifying agent of the formula I.

DETAILED DESCRIPTION OF THE INVENTION

Adding from 0.1 to 5 weight percent, and preferably from 0.5 to 4 weight percent of a borated sulfur-containing 1,2-alkane diol of the Formula I to a crankcase lubricating oil significantly improves the fuel economy of the internal combustion engine. Specifically, improvements in fuel mileage of about 2% on the average have been observed in engine tests. This fuel economy improvement can be obtained in both compression-ignition engines, that is, diesel engines, and spark-ignition engines, that is, gasoline engines.

The borated sulfur-containing 1,2-alkane diols are prepared by borating a sulfur-containing 1,2-alkane diol of the formula

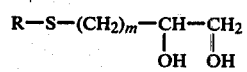

wherein R and m are as defined above, with a stoichiometric amount of boric acid with removal of the water of reaction by azeotropic distillation. The reaction is believed to proceed according to the following scheme:

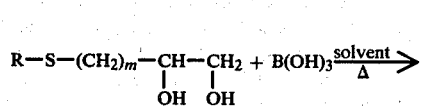

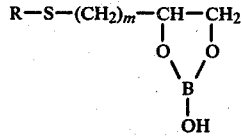

where R and m are as defined above.

The reaction may be carried out at a temperature in the range of 60° C. to 135° C., in the presence of any suitable organic solvent such as methanol, benzene, xylenes, toluene, neutral oil and the like. If the solvent does not form an azeotrope with water, enough of an azeotropic forming agent is included to remove water azeotropically.

In the above Formula I, R can be a straight chain, branch chain, primary, secondary or tertiary alkyl group. Examples of suitable groups are n-pentyl, n-octyl, n-dodecyl, 2-ethyldecyl, n-eccosyl, 1-ethyl eicosyl, n-dodocyl, n-tricontyl and the like.

The preferred compounds of the Formula I are those wherein R is alkyl containing 5 to 18 carbon atoms, and m is 1.

The sulfur-containing 1,2-alkane diols are readily made by conventional methods. For example, a mercaptan of the Formula II, RSH wherein R is defined above, may be reacted with a dihydroxyalkyl halide of the Formula III

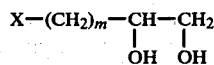

wherein X is chloro or bromo and m is as described above, in a suitable solvent such as methanol at reflux temperatures according to the following scheme:

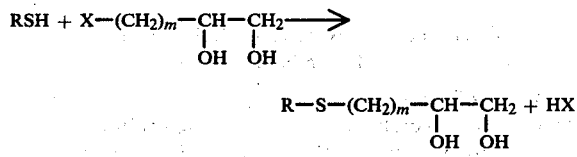

Compounds wherein m is 1 may also be prepared by reacting a mercaptan of the Formula II with glycidol at about 100° C. in the presence of a trialkylamine catalyst such as triethylamine. Alternatively, these latter compounds may be prepared by reacting the potassium mercaptide of alpha-thioglycerine with the appropriate alkyl iodide or bromide according to procedures described by R. L. Shriner et al, J. Am. Chem. Soc., 52, 2066 (1930) and D. David Lawson et al, J. Org. Chem., 26,615-16 (1961).

Examples of the preferred sulfur-containing 1,2-alkane diols which may be borated are 4-thia-1,2-hexadecane diol, 5-thia-1,2-hexadecane diol, 5-thia-1,2-heptadecane diol, 4-thia-1,2-heptadecane diol and 4-thia-1,2-octadecane diol.

The lubricating oils used in the process of this invention contain a major amount of a lubricating oil and from about 0.10 to 5.0 weight percent of the borated sulfur-containing 1,2-alkane diol of Formula I, preferably, from 0.5 to 4.0 weight percent, and most preferably, 1 to 2 weight percent based on the weight of the total composition. The optimum amount of borated sulfur-containing 1,2-alkane diol within these ranges will vary slightly depending on the base oil and other additives present in the oil.

Additive concentrates are also included within the scope of this invention. In the concentrate additive form, borated sulfur-containing 1,2-alkane diol is present in a concentration ranging from 5 to 50 weight percent.

The lubricating compositions are prepared by admixing, using conventional techniques, the appropriate amount of the desired borated sulfur-containing 1,2-alkane diol of the Formula I with the lubricating oil.

When concentrates are being prepared, the amount of hydrocarbon oil is limited, but is sufficient to dissolve the required amount of borated sulfur-containing 1,2-alkane diol. Generally, the concentrate will have sufficient borated sulfur-containing 1,2-alkane diol to permit subsequent dilution with 1- to 10-fold more lubricating oil.

As another embodiment of this invention, the lubricating oils to which the borated sulfur-containing 1,2-alkane diols of the Formula I are added contain an alkali or alkaline earth metal hydrocarbyl sulfonate, an alkali or alkaline earth metal phenate or mixtures thereof, Group II metal salt dihydrocarbyl dithiophosphate and an alkenyl succinimide or succinate or mixtures thereof.

The alkali or alkaline earth metal hydrocarbyl sulfonates may be either petroleum sulfonate, synthetically alkylated aromatic sulfonates, or aliphatic sulfonates such as those derived from polyisobutylene. One of the more important functions of the sulfonates is to act as a detergent and dispersant. These sulfonates are well known in the art. The hydrocarbyl group must have a sufficient number of carbon atoms to render the sulfonate molecule oil soluble. Preferably, the hydrocarbyl portion has at least 20 carbon atoms and may be aromatic or aliphatic, but is usually alkylaromatic. Most preferred for use are calcium, magnesium or barium sulfonates which are aromatic in character.

Certain sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

The sulfonates may be neutral or overbased having base numbers up to about 400 or more. Carbon dioxide is the most commonly used material to produce the basic or overbased sulfonates. Mixtures of neutral and overbased sulfonates may be used. The sulfonates are ordinarily used so as to provide from 0.3% to 10% by weight of the total composition. Preferably, the neutral sulfonates are present from 0.4% to 5% by weight of the total composition and the overbased sulfonates are present from 0.3% to 3% by weight of the total composition.

The phenates for use in this invention are those conventional products which are the alkali or alkaline earth metal salts of alkylated phenols. One of the functions of the phenates is to act as a detergent and dispersant. Among other things, it prevents the deposit of contaminants formed during high temperature operation of the engine. The phenols may be mono- or polyalkylated.

The alkyl portion of the alkylphenate is present to lend oil solubility to the phenate. The alkyl portion can be obtained from naturally occurring or synthetic sources. Naturally occurring sources include petroleum hydrocarbons such as white oil and wax. Being derived from petroleum, the hydrocarbon moiety is a mixture of different hydrocarbyl groups, the specific composition of which depends upon the particular oil stock which was used as a starting material. Suitable synthetic sources include various commercially available alkenes and alkane derivatives which, when reacted with the phenol, yield an alkylphenol. Suitable radicals obtained include butyl, hexyl, octyl, decyl, dodecyl, hexadecyl, eicosyl, tricontyl, and the like. Other suitable synthetic sources of the alkyl radical include olefin polymers such as polypropylene, polybutylene, polyisobutylene and the like.

The alkyl group can be straight-chained or branch-chained, saturated or unsaturated (if unsaturated, preferably containing not more than 2 and generally not more than 1 site of olefin unsaturation). The alkyl radicals will generally contain from 4 to 30 carbon atoms. Generally when the phenol is monoalkyl-substituted, the alkyl radical should contain at least 8 carbon atoms. The phenate may be sulfurized if desired. It may be either neutral or overbased and if overbased will have a base number of up to 200 to 300 or more. Mixtures of neutral and overbased phenates may be used.

The phenates are ordinarily present in the oil to provide from 0.2% to 27% by weight of the total composition. Preferably, the neutral phenates are present from 0.2% to 9% by weight of the total composition and the overbased phenates are present from 0.2 to 13% by weight of the total composition. Most preferably, the overbased phenates are present from 0.2% to 5% by weight of the total composition. Preferred metals are calcium, magnesium, strontium or barium.

The sulfurized alkaline earth metal alkylphenates are preferred. These salts are obtained by a variety of processes such as treating the neutralization product of an alkaline earth metal base and an alkylphenol with sulfur. Conveniently the sulfur, in elemental form, is added to the neutralization product and reacted at elevated temperatures to produce the sulfurized alkaline earth metal alkylphenate.

If more alkaline earth metal base were added during the neutralization reaction than was necessary to neutralize the phenol, a base sulfurized alkaline earth metal alkylphenate is obtained. See, for example, the process of Walker et al, U.S. Pat. No. 2,680,096. Additional basicity can be obtained by adding carbon dioxide to the basic sulfurized alkaline earth metal alkylphenate. The excess alkaline earth metal base can be added subsequent to the sulfurization step but is conveniently added at the same time as the alkaline earth metal base is added to neutralize the phenol.

Carbon dioxide is the most commonly used material to produce the basic or "overbased" phenates. A process wherein basic sulfurized alkaline earth metal alkylphenates are produced by adding carbon dioxide is shown in Hanneman, U.S. Pat. No. 3,178,368.

The Group II metal salts of dihydrocarbyl dithiophosphoric acids exhibit wear, antioxidant and thermal stability properties. Group II metal salts of phosphorodithioic acids have been described previously. See, for example, U.S. Pat. No. 3,390,080, columns 6 and 7, wherein these compounds and their preparation are described generally. Suitably, the Group II metal salts of the dihydrocarbyl dithiophosphoric acids useful in the lubricating oil composition of this invention contain from about 4 to about 12 carbon atoms in each of the hydrocarbyl radicals and may be the same or different and may be aromatic, alkyl or cycloalkyl. Preferred hydrocarbyl groups are alkyl groups containing from 4 to 8 carbon atoms and are represented by butyl, isobutyl, sec.-butyl, hexyl, isohexyl, octyl, 2-ethylhexyl and the like. The metals suitable for forming these salts include barium calcium, strontium, zinc and cadmium, of which zinc is preferred.

Preferably, the Group II metal salt of a dihydrocarbyl dithiophosphoric acid has the following formula:

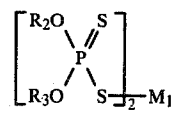

wherein:

$R_2$ and $R_3$ each independently represent hydrocarbyl radicals as described above, and $M_1$ represents a Group II metal cation as described above.

The dithiophosphoric salt is present in the lubricating oil compositions of this invention in an amount effective to inhibit wear and oxidation of the lubricating oil. The amount ranges from about 0.1 to about 4 percent by weight of the total composition, preferably the salt is present in an amount ranging from about 0.2 to about 2.5 percent by weight of the total lubricating oil composition. The final lubricating oil composition will ordinarily contain 0.025 to 25% by weight phosphorus and preferably 0.05 to 15% by weight.

The alkenyl succinimide or succinate or mixtures thereof are present to, among other things, act as a dispersant and prevent formation of deposits formed during operation of the engine. The alkenyl succinimides and succinates are well known in the art. The alkenyl succinimides are the reaction product of a polyolefin polymer-substituted succinic anhydride with an amine, preferably a polyalkylene polyamine, and the alkenyl succinates are the reaction product of a polyolefin polymer-substituted succinic anhydride with monohydric and polyhydric alcohols, phenols and naphthols, preferably a polyhydric alcohol containing at least three hydroxy radicals. The polyolefin polymer-substituted succinic anhydrides are obtained by reaction of a polyolefin polymer or a derivative thereof with maleic anhydride. The succinic anhydride thus obtained is reacted with the amine or hydroxy compound. The preparation of the alkenyl succinimides has been described many times in the art. See, for example, U.S. Pat. Nos. 3,390,082, 3,219,666 and 3,172,892, the disclosure of which are incorporated herein by reference. The preparation of the alkenyl succinates has also been described in the art. See, for example, U.S. Pat. Nos. 3,381,022 and 3,522,179, the disclosures of which are incorporated by reference.

Particularly good results are obtained with the lubricating oil compositions of this invention when the alkenyl succinimide or succinate is a polyisobutene-substituted succinic anhydride of a polyalkylene polyamine or polyhydric alcohol, respectively.

The polyisobutene from which the polyisobutene-substituted succinic anhydride is obtained by polymerizing isobutene and can vary widely in its compositions. The average number of carbon atoms can range from 30 or less to 250 or more, with a resulting number average molecular weight of about 400 or less to 3,000 or more. Preferably, the average number of carbon atoms per polyisobutene molecule will range from about 50 to about 100 with the polyisobutenes having a number average molecular weight of about 600 to about 1,500. More preferably, the average number of carbon atoms per polyisobutene molecule ranges from about 60 to about 90, and the number average molecular weight ranges from about 800 to 1,300. The polyisobutene is reacted with maleic anhydride according to well-known procedures to yield the polyisobutene-substituted succinic anhydride.

In preparing the alkenyl succinimide, the substituted succinic anhydride is reacted with a polyalkylene polyamine to yield the corresponding succinimide. Each alkylene radical of the polyalkylene polyamine usually has up to about 8 carbon atoms. The number of alkylene radicals can range up to about 8. The alkylene radical is exemplified by ethylene, propylene, butylene, trimethylene, tetramethylene, pentamethylene, hexamethylene, octamethylene, etc. The number of amino groups generally, but not necessarily, is one greater than the number of alkylene radicals present in the amine, i.e., if a polyalkylene polyamine contains 3 alkylene radicals, it will usually contain 4 amino radicals. The number of amino radicals can range up to about 9. Preferably, the alkylene radical contains from about 2 to about 4 carbon atoms and all amine groups are primary or secondary. In this case, the number of amine groups exceeds the number of alkylene groups by 1. Preferably the polyalkylene polyamine contains from 3 to 5 amine groups. Specific examples of the polyalkylene polyamines include ethylenediamine, diethylenetriamine, triethylenetetramine, propylenediamine, tripropylenetetramine, tetraethylenepentamine, trimethylenediamine, pentaethylenehexamine, di-(trimethylene)triamine, tri(hexamethylene)tetramine, etc.

Other amines suitable for preparing the alkenyl succinimide useful in this invention include the cyclic amines such as piperizine, morpholine and dipiperizines.

Preferably the alkenyl succinimides used in the compositions of this invention have the following formula:

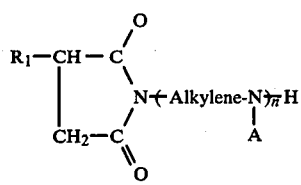

I wherein:
a. $R_1$ represents an alkenyl group, preferably a substantially saturated hydrocarbon prepared by polymerizing aliphatic monoolefins. Preferably $R_1$ is prepared from isobutene and has an average number of carbon atoms and a number average molecular weight as described above;

b. the "Alkylene" radical represents a substantially hydrocarbyl group containing up to about 8 carbon atoms and preferably containing from about 2 to 4 carbon atoms as described hereinabove;

c. A represents a hydrocarbyl group, an amine-substituted hydrocarbyl group, or hydrogen. The hydrocarbyl group and the amine-substituted hydrocarbyl groups are generally the alkyl and amino-substituted alkyl analogs of the alkylene radicals described above. Preferably A represents hydrogen;

d. n represents an integer of from about 1 to 10, and preferably from about 3 to 5.

The alkenyl succinimide can be reacted with boric acid or a similar boron-containing compound to form borated dispersants having utility in this invention. The borated succinimides are intended to be included within the scope of the term "alkenyl succinimide".

The alkenyl succinates are those of the above-described succinic anhydride with hydroxy compounds which may be aliphatic compounds such as monohydric and polyhydric alcohols or aromatic compounds such as phenols and naphthols. The aromatic hydroxy compounds from which the esters may be derived are illustrated by the following specific examples: phenol, beta-naphthol, alpha-naphthol, cresol, resorcinol, catehol, p,p'-dihydroxybiphenyl, 2-chlorophenol, 2,4-dibutylphenol, propene tetramer-substituted phenol, didodecylphenol, 4,4'-methylene-bis-phenol, alpha-decyl-beta-naphthol, polyisobutene(molecular weight of 1000)-substituted phenol, the condensation product of heptylphenol with 0.5 mole of formaldehyde, the condensation product of octylphenol with acetone, di(hydroxyphenyl)oxide, di(hydroxyphenyl)sulfide, di(hydroxyphenyl)disulfide, and 4-cyclohexylphenol. Phenol and alkylated phenols having up to three alkyl substituents are preferred. Each of the alkyl substituents may contain 100 or more carbon atoms.

The alcohols from which the esters may be derived preferably contain up to about 40 aliphatic carbon atoms. They may be monohydric alcohols such as methanol, ethanol, isooctanol, dodecanol, cyclohexanol, cyclopentanol, behenyl alcohol, hexatriacontanol, neopentyl alcohol, isobutyl alcohol, benzyl alcohol, beta-phenylethyl alcohol, 2-methylcyclohexanol, beta-chloroethanol, monomethyl ether of ethylene glycol, monobutyl ether of ethylene glycol, monopropyl ether of diethylene glycol, monododecyl ether of triethylene glycol, monooleate of ethylene glycol, monostearate of diethylene glycol, secpentyl alcohol, tert-butyl alcohol, 5-bromo-dodecanol, nitro-octadecanol and dioleate of glycerol. The polyhydric alcohols preferably contain from 2 to about 10 hydroxy radicals. They are illustrated by, for example, ethylene glycol, diethylene glycol, triethylene glycol, tetraethylene glycol, dipropylene glycol, tripropylene glycol, dibutylene glycol, tributylene glycol, and other alkylene glycols in which the alkylene radical contains from 2 to about 8 carbon atoms. Other useful polyhydric alcohols include glycerol, monooleate of glycerol, monomethyl ether of glycerol, pentraerythritol, 9,10-dihydroxy stearic acid, methyl ester of 9,10-dihydroxy stearic acid, 1,2-butanediol, 2,3-hexanediol, 2,4-hexanediol, pinacol, erythritol, arabitol, sorbitol, mannitol, 1,2-cyclohexanediol, and xylene glycol. Carbohydrates such as sugars, starches, cellulose, etc., likewise may yield esters. The carbohydrates may be exemplified by a glucose, fructose, sucrose, rhamnose, mannose, glyceraldehyde, and galactose.

An especially preferred class of polyhydric alcohols are those having at least three hydroxy radicals, some of which have been esterified with a monocarboxylic acid having from about 8 to about 30 carbon atoms such as octanoic acid, oleic acid, stearic acid, linoleic acid, dodecanoic acid, or tall oil acid. Examples of such partially esterified polyhydric alcohols are the monooleate of sorbitol, distearate of sorbitol, monooleate of glycerol, monostearate of glycerol, di-dodecanoate of erythritol.

The esters may also be derived from unsaturated alcohols such as allyl alcohol, cinnamyl alcohol, propargyl alcohol, 1-cyclohexene-3-ol, an oleyl alcohol. Still other classes of the alcohols capable of yielding the esters of this invention comprises the ether-alcohols and amino-alcohols including, for example, the oxyalkylene-, oxy-arylene-, amino-alkylene-, and amino-arylene-substituted alcohols having one or more oxy-alkylene, amino-alkylene or amino-arylene oxy-arylene radicals. They are exemplified by Cellosolve, carbitol, phenoxyethanol, heptylphenyl-(oxypropylene)$_6$-H, octyl(oxyethylene)$_{30}$-H, phenyl(oxyoctylene)$_2$-H, mono(heptylphenyl-oxypropylene)-substituted glycerol, poly(styrene oxide), amino-ethanol, 3-amino ethyl-pentanol, di(hydroxyethyl)amine, p-aminophenol, tri(hydroxypropyl)amine, N-hydroxyethyl ethylene diamine, N,N,N',N'-tetrahydroxytrimethylene diamine, and the like. For the most part, the ether-alcohols having up to about 150 oxy-alkylene radicals in which the alkylene radical contains from 1 to about 8 carbon atoms are preferred.

The esters may be di-esters of succinic acids or acidic esters, i.e., partially esterified succinic acids, as well as partially esterified polyhydric alcohols or phenols, i.e., esters having free alcoholic or phenolic hydroxyl radicals. Mixtures of the above-illustrated esters likewise are contemplated within the scope of the invention.

The alkenyl succinates can be reacted with boric acid or a similar boron-containing compound to form borated dispersants having utility in this invention. Such borated succinates are described in U.S. Pat. No. 3,533,945, the disclosure of which is incorporated herein by reference. The borated succinates are intended to be included within the scope of the term "alkenyl succinate."

The alkenyl succinimide and succinates are present in the lubricating oil compositions of the invention in an amount effective to act as a dispersant and prevent the deposit of contaminants formed in the oil during operation of the engine. The amount of alkenyl succinimide and succinates can range from about 1 percent to about 20 percent weight of the total lubricating oil composition. Preferably the amount of alkenyl succinimide or succinate present in the lubricating oil composition of the invention ranges from about 1 to about 10 percent by weight of the total composition.

The finished lubricating oil may be single or multigrade. Multigrade lubricating oils are prepared by adding viscosity index (VI) improvers. Typical viscosity index improvers are polyalkyl methacrylates, ethylene propylene copolymers, styrene diene copolymers and the like. So-called decorated VI improvers having both viscosity index and dispersant properties are also suitable for use in the formulations of this invention.

The lubricating oil used in the compositions of this invention may be mineral oil or in synthetic oils of viscosity suitable for use in the crankcase of an internal combustion engine. Crankcase lubricating oils ordinarily have a viscosity of about 1300 cst 0° F. to 22.7 cst at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_{6-12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Other additives which may be present in the formulation include rust inhibitors, foam inhibitors, corrosion inhibitors, metal deactivators, pour point depressants, antioxidants, and a variety of other well-known additives.

The following examples are offered to specifically illustrate the invention. These examples and illustrations are not to be construed in any way as limiting the scope of the invention.

EXAMPLE 1

A two-liter reaction flask was charged with 404.82 gms (2 moles) of dodecanethiol and 148.16 gms (2 moles) of glycidol. The reaction mixture was stirred and heated to 70° C. after which 5 gms triethylamine was added. The temperature rose rapidly to 210° C. and the reaction mixture was cooled slowly to 70° C. and stirred for 1 hour. The final product, 4-thia-1,2-hexadecanediol, is filtered hot through Celite. Product yield was 556.78 gms.

In a similar manner, 4-thia-1,2-heptadecane diol and 4-thia-1,2-octadecane diol are prepared by substituting an equivalent amount of tridecanethiol and tetradecanethiol, respectively for dodecanethiol in the above procedure.

In an alternative method, 4-thia-1,2-hexadecane diol may be prepared as follows.

To 110 gms (1 mole) of alpha-chloro glycerine is added 44 gms (0.6 mole) or slaked lime in 100 ml. methanol. The reaction mixture is heated to reflux with stirring and 202 gms (1 mole) dodecanethiol is added over 0.5 hour. The reaction mixture is allowed to stir for another 1 hour after which the methanol is removed and the product is filtered hot through celite.

In a similar manner, 5-thia-1,2-hexadecane diol is prepared by substituting an equivalent amount of 4-chloro-1,2-butane diol for alpha-chloro glycerine in the above procedure.

Also, 5-thia-1,2-heptadecane diol may be prepared by substituting equivalent amounts of tridecanethiol and 4-chloro-1,2-butane diol for dodecanethiol and alpha-chloro glycerine in the above procedure.

EXAMPLE 2

A 3-liter flask was charged with 691 gms (2.5 moles) 4-thia-1,2-hexadecane diol and heated with stirring to 110° C. To the reaction flask was added 750 ml toluene and 169.95 gms (2.75 moles) of boric acid. The reaction mixture was heated for about 88 hours at azeotrope (90° to 120° C.) collecting about 121 ml. water. The product was filtered hot through celite, stripped on a roto-vacuum for one-half hour at 135° C. at 2 mm Hg, and stored under nitrogen. Product weight was 672.51 gm; % Boron found 3.50% (3.581 theory).

In a similar manner, 4-thia-1,2-heptadecane diol, 5-thia-1,2-hexadecane diol, 5-thia-1,2-heptadecane diol and 4-thia-1,2-octadecane diol may be borated by substituting equivalent amounts of each of these diols for the 4-thia-1,2-hexadecane diol in the above procedure.

EXAMPLE 3

In this test a Ford 302 V-8 engine was run on dynamometers with lubricating oil with and without the borated sulfur-containing alkane diols.

The engine was run under the following operating conditions:

3000 RPM
9.5" Hg manifold pressure (absolute)
195° F. H$_2$O out temperature
200° F. Oil gallery temperature.

This test was run under constant conditions with a base oil CC350N containing 200 mmoles/kg. of overbased sulfurized calcium polypropylene phenate and 60 mmoles/kg of zinc di(isobutyl/mixed primary hexyl)dithiophosphate and then with the same base oil containing 2% by weight of borated 4-thia-1,2-hexadecane diol prepared according to Example 2. The oil compositions of this invention containing the borated sulfur-containing alkane diol was found to reduce fuel consumption of the engine an average of 2.0% ±0.2.

Also, formulated crankcase oils each containing 2% by weight of borated 5-thia-1,2-heptadecane diol, borated 4-thia-1,2-heptadecane diol, or 4-thia-1,2-octadecane diol in place of borated 4-thia-1,2-hexadecane diol in the above formulation are also effective in reducing fuel consumption in an internal combustion engine.

A fully formulated oil (Chevron 20N/80N) containing 2% of borated 4-thia-1,2-hexadecane diol of Example 1, 3.5% of a polyisobutenyl succinimide of tetraethylenepentamine, 30 mmols/kg overbased magnesium hydrocarbyl sulfonate, 20 mmols/kg of overbased sulfurized calcium polypropylene phenate, 18 mmols/kg zinc O,O-di(2-ethylhexyl) dithiophosphate, and 5.5% of a polymethacrylate-based VI improver is effective in reducing fuel consumption in an internal combustion engine.

I claim:

1. A borated sulfur-containing 1,2-alkane diol of the formula

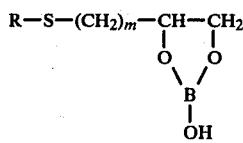

wherein R is alkyl containing 5 to 30 carbon atoms and m is 1 or 2.

2. The compound of claim 1 wherein R is alkyl containing 5 to 18 carbon atoms.

3. The compound of claim 1 wherein R is alkyl containing from 5 to 18 carbon atoms, m is 1.

4. The compound of claim 1 wherein the borated sulfur-containing 1,2-alkane diol is borated 4-thia-1,2-hexadecane diol, borated 5-thia-1,2-hexadecane diol, borated 5-thia-1,2-heptadecane diol, borated 4-thia-1,2-heptadecane diol or borated 4-thia-1,2-octadecane diol.

5. The compound of claim 4 wherein the borated sulfur-containing 1,2-alkane diol is borated 4-thia-1,2-hexadecane diol.

6. The lubricating oil composition comprising a major proportion of an oil of lubricating viscosity and a minor effective amount of a borated sulfur-containing 1,2-alkane diol friction-reducing additive of the formula

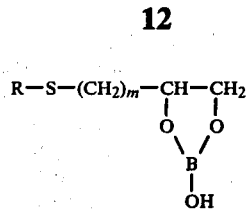

wherein R is aklyl containing from 5 to 30 carbon atoms, m is 1 or 2.

7. The composition of claim 1 containing from about 0.1 to 5% of said additive.

8. The lubricating oil composition of claim 6 where R is alkyl containing 5 to 18 carbon atoms.

9. The lubricating oil composition of claim 6 wherein R is alkyl containing from 5 to 18 carbon atoms, m is 1.

10. The lubricating oil composition of claim 6 wherein the borated sulfur-containing 1,2-alkane diol additive is borated 4-thia-1,2-hexadecane diol, borated 5-thia-1,2-hexadecane diol, borated 5-thia-1,2-heptadecane diol, borated 4-thia-1,2-heptadecane diol, or borated 4-thia-1,2-octadecane diol.

11. The lubricating oil composition of claim 10 wherein the borated sulfur-containing 1,2-alkane diol additive is borated 4-thia-1,2-hexadecane diol.

12. The lubricating oil composition formulated for use in the crankcase of an internal combustion engine in order to improve the fuel comsumption of said engine comprising
 (a) a major amount of an oil of lubricating viscosity; and
 (b) an effective amount of each of the following:
  1. from 1%–20% of an ankenyl succinimide or alkenyl succinate or mixtures thereof,
  2. from 0.1%–4% of a Group II metal salt of a dihydrocarbyl dithiophosphoric acid,
  3. from 0.3%–10% of a neutral or overbased alkali or alkaline earth metal hydrocarbyl sulfonate or mixtures thereof,
  4. from 0.3%–27% of a neutral or overbased alkali or alkaline earth metal alkylated phenate, or mixtures thereof, and
  5. from 0.1%–5% of a borated sulfur-containing 1,2-alkane diol friction modifying agent of the formula:

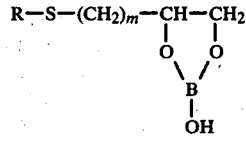

wherein R is alkyl containing from 5 to 30 carbon atoms, m is 1 or 2.

13. The lubricating oil composition of claim 12 wherein R is alkyl containing 5 to 18 carbon atoms.

14. The lubricating oil composition according to claim 12 wherein in the borated sulfur-containing 1,2-alkane diol, R is alkyl from 5 to 18 carbon atoms, m is 1.

15. The lubricating oil composition of claim 12 wherein the borated sulfur-containing 1,2-alkane diol friction reducing additive is borated 4-thia-1,2-hexadecane diol, borated 5-thia-1,2-hexadecane diol, borated 5-thia-1,2-heptadecane diol, borated 4-thia-1,2-heptadecane diol, or borated 5-thia-1,2-octadecane diol.

16. The lubricating oil composition according to claim 12 wherein (1) said alkenyl succinimide is a polyisobutenyl succinimide of a polyalkylene polyamine, and said alkenyl succinate is a polyisobutenyl succinate of a polyhydric alcohol;
(2) said metal salt of the dihydrocarbyl dithiophosphoric acid is zinc dialkyl dithiophosphate wherein the alkyl group contains from 4 to 12 carbon atoms;
(3) said metal of the neutral or overbased alkali or alkaline earth metal sulfonate is calcium, magnesium or barium or mixtures thereof;
(4) said metal of the neutral or overbased alkali or alkaline earth metal phenate is calcium, magnesium or barium;
(5) said R group of the borated sulfur-containing 1,2-alkane diol is alkyl containing from 5 to 30 carbon atoms, and m is 1.

17. The lubricating oil composition according to claim 16 wherein
(1) said alkenyl succinimide is a polyisobutenyl succinimide of triethylenetetramine or polyisobutenyl succinimide of tetraethylenepentamine, and said alkenyl succinate is a polyisobutenyl succinate of pentaerythritol;
(2) said metal salt of the dihydrocarbyl dithiophosphoric acid is zinc O,O-di(2-ethylhexyl)dithiophosphate, zinc O,O-di(isobutyl/mixed primary hexyl)dithiophosphate, or zinc O,O-di(sec-butyl/mixed secondary hexyl)dithiophosphate;
(3) said metal salt of the sulfonate is an overbased magnesium or calcium hydrocarbyl sulfonate;
(4) said metal salt of the phenate is an overbased sulfurized calcium or magnesium monoalkylated phenate,
(5) said R group of the borated sulfur-containing 1,2-alkane diol is an alkyl containing from 5 to 18 carbon atoms.

18. The lubricating oil composition according to claim 16 wherein the borated sulfur-containing 1,2-alkane diol additive is borated 4-thia-1,2-hexadecane diol.

19. A method for reducing the fuel consumption of an internal combustion engine by treating the moving surfaces thereof with a composition according to any one of claim 1 or 12.

* * * * *